United States Patent
Sakai et al.

(10) Patent No.: US 6,407,054 B2
(45) Date of Patent: Jun. 18, 2002

(54) SURFACTANT COMPOSITION

(75) Inventors: Takaya Sakai; Makio Tetsu; Makoto Kubo; Akira Fujiu, all of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/726,577

(22) Filed: Dec. 1, 2000

(30) Foreign Application Priority Data

Dec. 1, 1999 (JP) .......................................... 11-341649

(51) Int. Cl.[7] .......................... C11D 1/66; C11D 1/825; C11D 3/20
(52) U.S. Cl. ...................... 510/501; 510/336; 510/341; 510/342; 510/350; 510/352; 510/499; 510/501
(58) Field of Search ................................. 510/336, 341, 510/342, 350, 352, 499, 501

(56) References Cited

U.S. PATENT DOCUMENTS 3,932,296 A * 1/1976 Byth .......................... 252/148
4,370,174 A * 1/1983 Braithwaite, Jr. .............. 134/7

FOREIGN PATENT DOCUMENTS

| JP | 07194958 | 8/1995 |
| JP | 09137190 | 5/1997 |
| JP | 10339783 | 12/1998 |
| JP | 1180785 | 3/1999 |
| WO | WO 9412610 | 6/1994 |
| WO | WO 9606596 | 3/1996 |
| WO | WO 9744434 | 11/1997 |
| WO | WO 9800507 | 1/1998 |

* cited by examiner

*Primary Examiner*—Gregory Delcotto
(74) *Attorney, Agent, or Firm*—Birch, Stewart, Kolasch & Birch, LLP

(57) ABSTRACT

There is provided a surfactant composition for detergents, which has its high detergency and foamability within a broad pH region even in the presence of solids. It has its excellent foamability, thickening property, water solubility and stability. The composition contains a component (a) represented by the following formula (I) and at least one component (b) represented by the formula (II) and (III), in the total amount of 0.1 to 80% by weight, at the ratio of (a)/(b) by weight of from 99.9/0.1 to 70/30.

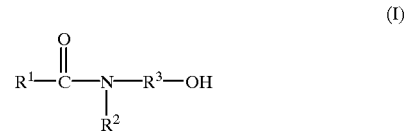

(I)

In the formula (I), $R^1CO-$ is a saturated or unsaturated acyl group which has 6 to 24 carbon atoms and which may have hydroxy group; $R^2$ is a linear or branched alkyl group having 1 to 3 carbon atoms; and $R^3$ is a linear or branched alkylene or alkenylene group having 1 to 6 carbon atoms.

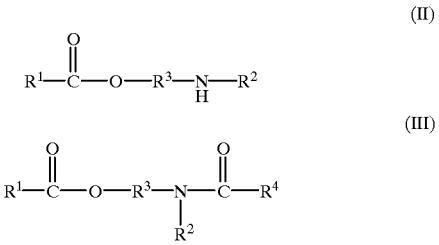

In the formula (II) and (III), $R^1CO-$, $R^2$ and $R^3$ have the same meanings as above and $R^4CO-$ is a saturated or unsaturated acyl group which has 6 to 24 carbon atoms and which may have a hydroxy group. The composition may also contain a surfactant other than the above-mentioned components (a) and (b).

7 Claims, No Drawings

SURFACTANT COMPOSITION

TECHNICAL FIELD OF THE INVENTION

The present invention relates to a surfactant composition for detergents having an excellent detergency to an oily stain and an abundant foamability. It has its excellent foamability, thickening property, water solubility and stability.

PRIOR ART

Not only a high detergency but also an abundant foaming are requested to a detergent such as a shampoo, a rinse, a solid soap, a body shampoo, a detergent for kitchens, a detergent for clothing and a detergent for dwellings. One which has been widely used as a main base in many products is an anionic surfactant such as an alkyl benzenesulfonate, an alkyl sulfate salt, a polyoxyethylene alkyl sulfate salt and an alkyl phosphate salt. However, although any thereof usually shows its excellent detergency and foaming, there is a problem therein that, when solids, a stain derived from silicone or the like is present, the detergency and foamability significantly lower.

In order to improve such a lowering in detergency and/or foamability, various co-surfactants besides the main base have been investigated. There have been first proposed a fatty acid diethanolamide which has been actually and widely used in the products and then proposed in recent years a fatty acid monoethanolamide (WO 98/00507, WO 97/44436, JP-A 11-80785, etc.), a nonionic surfactant based on a sugar amide (WO 94/12610), an acylated sarcosine (WO 96/06596), etc.

However, although these detergent compositions are improved in detergency and foamability, they are not well satisfactory yet. Moreover, since the detergents described above directly contact with the skin daily, they are demanded to exhibit a high performance at a weakly acidic pH region which is mild to the skin. However, in the conventional surfactant system, there has been mentioned such a problem that, even when the foaming is good in from neutral to basic regions, foaming does not take place at all in an acidic region.

DISCLOSURE OF THE INVENTION

An object of the present invention is to provide a surfactant composition which has its high detergency and foamability within a broad pH region even in the presence of solids. It has its excellent foamability, thickening property, water solubility and stability even under the above-mentioned condition. It is useful as a detergent.

The present invention is a surfactant composition comprising a component (a) represented by the following formula (I) and at least one component (b) represented by the formulae (II) and (III), in the total amount of 0.1 to 80% by weight, at the ratio of (a)/(b) by weight of from 99.9/0.1 to 70/30.

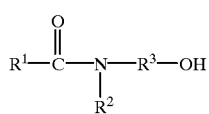

(I)

In the formula (I), $R^1CO-$ is a saturated or unsaturated acyl which has 6 to 24 carbon atoms and which may have a hydroxy group; is $R^2$ is a linear or branched alkyl group having 1 to 3 carbon atoms; and $R^3$ is a linear or branched alkylene group having 1 to carbon atoms or alkenylene group having 2 to 6 carbon atoms.

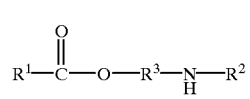

(II)

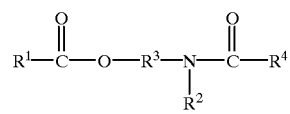

(III)

In the formulae (II) and (III), $R^1CO-$, $R^2$ and $R^3$ have the same meanings as above and $R^4CO-$ is a saturated or unsaturated acyl group which has 6 to 24 carbon atoms and which may have a hydroxy group.

The composition preferably comprises a surfactant other than the above-mentioned components (a) and (b).

It is also preferable that the ratio of the component (a) to the component (b), namely (a)/(b), by weight is from 99.99/0.01 to 80/20.

It is, further, preferable that the blending ratios of the compounds (I), (III) and (II) to their total amount are 80 to 99.99% by weight of the compound (I), 0.01 to 20% by weight of the compound (III) and 0 to 5% by weight of the compound (II).

The ratio of the blending amount of the components (a) and (b) in total to the blending amount of the surfactant other than the components (a) and (b) may be from 0.5/99.5 to 50/50 by weight.

The composition of the present invention may comprises glycerol as an essential component in an amount of 20% by weight or less as compared with the sum of the total amount of the components (a) and (b) and the amount of the surfactant other than the components (a) and (b).

The composition may comprise glycerol as an essential component in an amount of 20% by weight or less as compared with the sum of the total amount of the components (a) and (b) and the amount of the surfactant other than the components (a) and (b), provided that the ratio of the blending amount of the components (a) and (b) and glycerol in total to the blending amount of the surfactant other than the components (a) and (b) is from 0.5/99.5 to 50/50 by weight.

DETAILED DESCRIPTION OF THE INVENTION

In the component (a) of the present invention, $R^1CO-$ is an acyl group as mentioned above. A saturated or unsaturated acyl group having 8 to 18 carbon atoms is preferable. Among such an acyl group, one containing not less than 50% by weight of a fatty acid residue having 12 to 14 carbon atoms is preferable. Further, one in which a fatty acid residue having 12 carbon atoms is from not less than 40% by weight to less than 100% by weight is more preferable. Specific examples include acyl groups derived from octanoic acid, decanoic acid, dodecanoic acid, tetradecanoic acid, hexadecanoic acid, octadecanoic acid, docosanoic acid, linoleic acid, 2-ethylhexanoic acid, 2-octylundecanoic acid, isostearic acid, oleic acid, a coconut-fatty acid, a palm oil-fatty acid, a palm kernel oil-fatty acid, a beef tallow-fatty acid, etc. There are particularly preferable acyl groups derived from octanoic acid, decanoic acid, dodecanoic acid, tetradecanoic acid, hexadecanoic acid, octadecanoic acid, oleic acid, the coco-fatty acid, the palm oil-fatty acid, the palm kernel oil-fatty acid and the beef tallow-fatty acid.

In order not to lower the foamability, $R^2$ is a linear or branched alkyl group having 1 to 3 carbon atoms, preferably methyl group or ethyl group and particularly preferably methyl group. In addition, in order not to lower the surface-active performance, $R^3$ is a linear or branched alkylene or alkenylene group having 1 to 6 carbon atoms and preferably a linear or branched alkylene group having 2 or 3 carbon atoms.

Specific examples of the component (a), for instance, include N-(2-hydroxyethyl)-N-methyl octanamide, N-(2-hydroxyethyl)-N-methyl decanamide, N-(2-hydroxyethyl)-N-methyl dodecanamide, N-(2-hydroxyethyl)-N-methyl tertadecanamide, N-(2-hydroxyethyl)-N-methyl hexadecanamide, N-(2-hydroxyethyl)-N-methyl octadecanamide, N-(2-hydroxyethyl)-N-methyl-coco-fatty carboxamide, N-(2-hydroxyethyl)-N-methyl-palm kernel oil-fatty carboxamide, N-ethyl-N-(2-hydroxypropyl) dodecanamide, N-ethyl-N-(2-hydroxypropyl)oleamide and N-ethyl-N-(2-hydroxypropyl)isostearamide.

A method for producing the component (a) is not particularly limited. For example, it can be produced by a condensation reaction of a fatty acid or a fatty acid lower alcohol ester with an alkanolamine, by a reaction of a fatty acid halide with an alkanolamine in the presence of an alkaline catalyst, by an aminolysis of esters and an alkanolamine, or by the like. The product obtained by such a method often contains small amount of a fatty acid, an inorganic salt, glycerol and the like, but they does not affect the performances at all.

The component (b) is selected from the compounds represented by the above-mentioned formulae (II) and (III). However, it is not necessary to be single and two or more members may be mixed therein. $R^1CO$—, $R^2$ and $R^3$ in the formulae (II) and (III) have the same meanings as those in the formula (I). In each of the compounds, $R^1$, $R^2$ and $R^3$ may be same as or different from each other.

$R^4CO$— is a saturated or unsaturated acyl group which has 6 to 24 carbon atoms, preferably 8 to 18 carbon atoms, and which may have a hydroxy group. $R^1CO$— and $R^4CO$— may be the same or different. Specific examples and preferable ones for $R^4CO$— include those mentioned hereinabove for $R^1CO$—.

Specific examples of the compound represented by the formula (II), for instance, include 2-(methylamino)ethyl octanoate, 2-(methylamino)ethyl decanoate, 2-(methylamino)-ethyl dodecanoate, 2-(methylamino)ethyl tetradecanoate, 2-(methylamino)ethyl hexadecanoate, 2-(methylamino)ethyl octadecanoate, 2-(methylamino)ethyl oleate, 2-(ethylamino)ethyl octanoate, 2- (ethylamino)ethyl dodecanoate, 2-(ethylamino)ethyl tetradecanoate, 2-(ethylamino)ethyl hexadecanoate, 2-(ethylamino)ethyl octadecanoate, 2-(ethylamino)ethyl oleate, 2-(methylamino) propyl octanoate, 2-(methylamino)propyl decanoate, 2-(methylamino)propyl dodecanoate, 2-(methylamino) propyl tetradecanoate, 2-(methylamino)propyl hexadecanoate, 2-(methylamino)propyl octadecanoate, 2-(methylamino)propyl oleate and a (2-methylaminoethyl) coco-fatty carboxylate.

Further, (2-methylaminoethyl) coco-fatty carboxylate, (2 -methylaminoethyl) palm kernel oil-fatty carboxylate and the like are also included in (II).

Specific examples of the compound represented by the formula (III), for instance, include N-octanoyl-N-methylaminoethyl octanoate, N-octanoyl-N-methylaminoethyl decanoate, N-octanoyl-N-[2-(methylamino)ethyl]dodecanoate, N-octanoyl-N-[2-(methylamino)ethyl]tetradecanoate, N-octanoyl-N-[2-(methylamino)ethyl]hexadecanoate, N-octanoyl-N-[2-(methylamino)ethyl]octadecanoate, N-dodecanoyl-N-[2-(methylamino)ethyl]octanoate, N-dodecanoyl-N-[2-(methylamino)ethyl]decanoate, N-dodecanoyl-N-[2-(methylamino)ethyl]dodecanoate, N-dodecanoyl-N-[2-(methylamino)ethyl]tetradecanoate, N-dodecanoyl-N-[2-(methylamino)ethyl]hexadecanoate, N-dodecanoyl-N-[2-(methylamino)ethyl]octadecanoate, N-dodecanoyl-N-[6-(ethylamino)hexyl]octanoate, N-dodecanoyl-N-[6-(ethylamino)hexyl]decanoate, N-dodecanoyl-N-[6-(ethylamino)hexyl]dodecanoate, N-dodecanoyl-N-[6-(ethylamino)hexyl]tetradecanoate, N-dodecanoyl-N-[6-(ethylamino)hexyl]hexadecanoate, N-dodecanoyl-N-[6-(ethylamino)hexyl]octadecanoate, an (N-cocoyl-N-methylaminoethyl) coco-fatty carboxylate and an (N-palm kerneloyl-N-methylaminoethyl) palm kernel-fatty carboxylate.

The total amount of the components (a) and (b) in the composition of the present invention is 0.1 to 80% by weight and preferably 0.1 to 10% by weight in view of water solubility, stability of the product and foamability.

Further, the blending ratio of the component (a) to the component (b), namely (a)/(b), by weight is from 99.9/0.1 to 7 70/30, preferably from 98/2 to 70/30, more preferably from 98/2 to 90/10 and most preferably from 98/2 to 95/5 in view of water solubility, stability of the product and foamability.

The blending ratio of the component (a) to the component (b), namely (a) /(b), by weight in the composition of the present invention may be from 99.99/0.01 to 80/20 and preferably from 98/2 to 90/10 in view of foamability, thickening property and stability.

The composition of the present invention, comprising the components (a) and (b), has its high detergency and foamability and, if it further comprises a surfactant other than the components (a) and (b), the detergency and foamability are able to be further improved due to a synergism.

With regard to the blending ratio of the compounds (I), (III) and (II) in the composition of the present invention to their total amounts, the compound (I) is preferably 80 to 99.99% by weight and more preferably 90 to 98% by weight, the compound (III) is preferably 0.01 to 20% by weight and more preferably 2 to 10% by weight, and the compound (II) is preferably 0 to 5% by weight in view of obtaining a good surface-active performance.

In the surfactant composition of the present invention, very high foamability and thickening performance are exhibited when the components (a) and (b) are used together with a surfactant other than the components (a) and (b) (hereinafter, referred to as "other surfactant"). The total amount of the components (a) and (b) in the surfactant composition of the present invention can be optionally selected depending upon characters of the other surfactant. Further, in view of water solubility, stability, foamability and thickening property, the ratio of the blending amount of the components (a) and (b) in total to the blending amount of the other surfactant is preferably from 0.5/99.5 to 50/50 by weight.

The surfactant which can be used together is not particularly limited. For example, it may be one or more selected from an anionic surfactant such as a soap, an alkyl sulfate, a polyoxyethylene alkyl sulfate, an alkyl phosphate salt, a polyoxyethylene alkyl phosphate and an alkyl benzenesulfonate; a cationic surfactant such as an alkyltrimethylammonium salt, a dialkyldimethylammonium salt, an alkyldimethylbenzalkonium salt, an alkyl dimethylamine oxide and an amidopropyl dimethylamine oxide; an amphoteric surfactant such as an amidopropyl dimethylcarbobetaine, an alkyl dimethylcarbobetaine and an alkyl dimethylhydroxysulfobetaine; and a nonionic surfactant such as a polyoxyethylene alkyl ether and an alkyl polyglucoside. Among them, at least one is preferably an anionic, cationic or amphoteric surfactant and, at least one anionic surfactant is particularly preferably co-present.

Particularly preferably, the other surfactant may be one or more selected from a sulfate-based or sulfonate-based surfactant such as an alkyl sulfate, a polyoxyethylene alkyl sulfate and an alkylbenzene sulfonate; an amine oxide such as an alkyldimethyl amine oxide and amidopropyldimethyl amine oxide; an amide group-containing betaine such as amidopropyl dimethylcarbobetaine.; etc. One thereamong or two or more thereamong can be used and it is preferable that one or more sulfate-based surfactants are co-present.

In the composition of the present invention, the ratio by weight of the components (a) and (b) to the other surfactant, namely [components (a) and (b))/(other surfactant], when the components are used together with the surfactants is preferably from 1/10 to 10/10 and more preferably from 1/10 to 1/3, in view of a synergism of detergent performance and foamability.

The surfactant composition of the present invention can be more improved in its viscosity, by that glycerol is further contained. The amount of glycerol to the sum of the total amount of the components (a) and (b) and the amount of the surfactant other than the components (a) and (b) is preferably not more than 20% by weight and more preferably from 0.01 to 15% by weight. When glycerol is contained, the ratio of the blending amount of the components (a) and (b) in total and glycerol to the blending amount of the other surfactant is preferably from 0.5/99.5 to 50/50 and more preferably from 1/99 to 25/75 by weight.

The detergent composition of the present invention can exhibit the particularly preferable performance when the pH range is from 4.0 to 11.0.

The surfactant composition of the present invention can exhibit the particularly preferable performance such as foamability and thickening property and is useful as a base for a detergent, when the pH range is from 4.0 to 11.0.

Use of the detergent composition of the present invention is not particularly limited and, for example, it is useful as a detergent such as a shampoo, a solid soap, a body shampoo, a detergent for kitchens, a detergent for clothing and a detergent for dwellings. For such use, the composition may be optionally blended with the other detergent component, a moisturizing component, an oil component, various pharmaceutical components, a preservative, a germicide, a sequestering agent, an antioxidant, a UV absorber, a perfume, a dye or the like which is essential for the product design. Further, the form of the product may be in any form such as liquid, solid, paste, cream and lotion (or emulsion).

EXAMPLES

Examples ①-1 to ①-9 and Comparative Examples ①-1 to ①-2

The components as shown below were used, various detergent compositions having the formulations as shown in Table ①-1 were prepared and their detergency were evaluated by the following methods. The results are shown in Table ①-1.

<Components>
Component (a)
Compound ①-1: N-(2-Hydroxyethyl)-N-methyl lauramide
Compound ①-2: N-(2-Hydroxyethyl)-N-methyl coco-fatty carboxamide
Compound ①-3: N-(2-Hydroxyethyl)-N-methyl palm kernel oil-fatty carboxamide
Component (b)
Compound ①-4: 2-(Methylamino)ethyl laurate
Compound ①-5: (2-Ethylaminoethyl) coco-fatty carboxylate
Compound ①-6: (2-Ethylaminoethyl) palm kernel-fatty carboxylate
Compound ①-7: N-Lauroyl-N-methylaminoethyl laurate
Compound ①-8: (N-Cocoyl-N-methylaminoethyl) coco-fatty carboxylate
Compound ①-9: (N-palm kerneloyl-N-methylaminoethyl) palm kernel-fatty carboxylate
Other Surfactants
LAS: Sodium long-chain alkyl($C_{12}$) benzenesulfonate
AS: Sodium laurylsulfate
AES: Sodium polyoxyethylene(3) laurylsulfate
AE: Polyoxyethylene(6) lauryl ether
LDMAO: Long-chain alkyl($C_{12}$) dimethylamine oxide
Other Components
Polyacrylic acid: average molecular weight of 10,000
AM: Sodium salt of a copolymer of acrylic acid/maleic acid (molar ratio of 7/3), average molecular weight of 70,000
Zeolite: Crystalline aluminosilicate, $M_2O.Al_2O_3.2SiO_2.2H_2O$, average particle diameter of 2 $\mu$m, ion-exchange capacity of 290 $CaCO_3$ mg/g
Common components: Comprising 0.5% by weight of a fluorescent component, 2.0% by weight of a mixed enzymatic component comprising SAVINASE® 12.0T type W (supplied by Novo Nordisk A/S), KAC-500G (supplied by Kao Corp.) and Termamyl 60T (supplied by Novo Nordisk A/S) at the ratio of 2:1:1 and Glauber's salt and being prepared so as to make the total amount of the composition 100% by weight by addition of the Glauber's salt.

<Method for Evaluating the Detergency>
(1) Preparation of an Artificially Stained Cloth An artificial stain solution having the following composition was adhered to cloth to prepare an artificially stained cloth. Adhesion of the artificial stain solution to the cloth was carried out using a gravure roll coater. A step for producing the artificially stained cloth by adhering the artificial stain solution to the cloth was carried out under the condition that the cell capacity of the gravure roll was 58 $cm^3/m^2$, the coating rate of 1.0 m/minute, drying at 100° C. and drying time of 1 minute. The cloth used was cotton shirting cloth #2003 (supplied by TANIGASHIRA SHOTEN). Composition of the artificial stain solution

| | |
|---|---|
| Lauric acid | 0.44% by weight |
| Myristic acid | 3.09% by weight |
| Pentadecanoic acid | 2.31% by weight |
| Palmitic acid | 6.18% by weight |
| Heptadecanoic acid | 0.44% by weight |
| Stearic acid | 1.57% by weight |
| Oleic acid | 7.75% by weight |
| Triolein | 13.06% by weight |
| n-Hexadecyl palmitate | 2.18% by weight |
| Squalene | 6.53% by weight |
| Liquid crystal of albumen lecithin | 1.94% by weight |
| Kanuma aka-tsuchi (red soil) | 8.11% by weight |
| Carbon black | 0.01% by weight |
| Tap water | Balance |

(2) Washing Condition and the Evaluating Method

The detergent composition was dissolved in 4° DH hard water to prepare a 0.06-% aqueous solution. 5 sheets of the above-produced artificially stained cloth having the area of 10 cm×10 cm were placed into 1 liter of the prepared aqueous detergent solution and washed at 100 rpm using a Terg-O-Tometer. The washing condition was as follows.
Washing Condition Washing time 10 minutes Concentration of the composition to be evaluated 0.067%

Temperature of solution 10° C.

Rinsing With tap water for 5 minutes

With regard to the detergency, reflectance at 550 nm of the unstained initial cloth and those of the stained cloth before and after washing were measured by a recording color meter (supplied by Shimadzu Corporation), then a detergent ratio (%) was calculated by the following formula. The mean value thereof for the 5 sheets was made as detergency.

$$\text{Detergent Ratio} = \frac{\text{Reflectance after washing} - \text{Reflectance before washing}}{\text{Reflectance of the initial cloth} - \text{Reflectance before washing}} \times 100$$

TABLE ①-1

| | | Example | | | | | | | | | Comparative Example | |
|---|---|---|---|---|---|---|---|---|---|---|---|---|
| | | ①-1 | ①-2 | ①-3 | ①-4 | ①-5 | ①-6 | ①-7 | ①-8 | ①-9 | ①-1 | ①-2 |
| Detergent composition (% by weight) | | | | | | | | | | | | |
| Component (a) | Compound ①-1 | 0.96 | 0.95 | 0.90. | 1.80 | 3.10 | | | 0.95 | | | |
| | Compound ①-2 | | | | | | 0.95 | | | | | |
| | Compound ①-3 | | | | | | | 0.95 | | 0.95 | | |
| Component (b) | Compound ①-4 | 0.04 | 0.03 | 0.05 | 0.13 | 0.40 | | | 0.03 | | | |
| | Compound ①-5 | | | | | | 0.03 | | | | | |
| | Compound ①-6 | | | | | | | 0.03 | | 0.03 | | |
| | Compound ①-7 | | 0.02 | 0.05 | 0.07 | 0.50 | | | 0.02 | | | |
| | Compound ①-8 | | | | | | 0.02 | | | | | |
| | Compound ①-9 | | | | | | | 0.02 | | 0.02 | | |
| Other surfactant | LAS | 19 | 19 | 19 | 18 | 16 | 19 | 19 | | | 20 | |
| | AS | | | | | | | | 9 | 9 | | 10 |
| | AES | | | | | | | | 10 | 10 | | 10 |
| | AE | 5 | 5 | 5 | 5 | 5 | 5 | 5 | | | 5 | |
| | LDMAO | | | | | | | | 5 | 5 | | 5 |
| Polyacrylic acid | | 2.5 | 2.5 | 2.5 | 2.5 | 2.5 | 2.5 | 2.5 | 2.5 | 2.5 | 2.5 | 2.5 |
| AM | | 2.5 | 2.5 | 2.5 | 2.5 | 2.5 | 2.5 | 2.5 | 2.5 | 2.5 | 2.5 | 2.5 |
| Sodium sulfite | | 1 | 1 | 1 | 1 | 1 | 1 | 1 | 1 | 1 | 1 | 1 |
| Potassium carbonate | | 4 | 4 | 4 | 4 | 4 | 4 | 4 | 4 | 4 | 4 | 4 |
| Sodium carbonate | | 15 | 15 | 15 | 15 | 15 | 15 | 15 | 15 | 15 | 15 | 15 |
| Sodium silicate | | 10 | 10 | 10 | 10 | 10 | 10 | 10 | 10 | 10 | 10 | 10 |
| Zeolite | | 20 | 20 | 20 | 20 | 20 | 20 | 20 | 20 | 20 | 20 | 20 |
| Common components | | balance | balance | balance | balance | balance | balance | balance | balance | balance | balance | balance |
| Detergent ratio (%) | | 57.3 | 58.3 | 59.1 | 59.8 | 54.5 | 54.8 | 57.6 | 55.3 | 55.6 | 50.1 | 48.5 |

Examples ①-10 to ①-16 and Comparative Examples ①-3 to ①-7

Various detergent compositions having the formulations as shown in Table ①-2 were prepared using the following components and their foamabilities were evaluated by the following method. The results are shown in Table ①-2.

<Components>

Compounds ①-1 to ①-9, AES and LDMAO have the same meanings as in Table ①-1.

LAPB: Lauroylamidopropyl dimethylcarbobetaine

DEA: Lauroyl diethanolamide

MEA: Lauroyl monoethanolamide

<Method for Evaluating the Foamability ①>

30 mL of an aqueous solution in which a detergent composition was diluted with deionized water to 20-fold were prepared and the pH was adjusted using citric acid. The aqueous solution was placed in a 300-mL messcylinder having an inner diameter of 3 cm equipped with a stop cock and shaken at 25° C. for 10 seconds with an amplitude of 10 cm for 20 times and the foam volume (mL) immediately thereafter and that after 5 minutes were measured. From the foam volume immediately thereafter, the foaming speed was evaluated while, from the foam volume after 5 minutes, the foaming sustentation-property was evaluated.

TABLE (1)-2

| | | Example | | | | | | | Comparative Example | | | | |
|---|---|---|---|---|---|---|---|---|---|---|---|---|---|
| | | (1)-10 | (1)-11 | (1)-12 | (1)-13 | (1)-14 | (1)-15 | (1)-16 | (1)-3 | (1)-4 | (1)-5 | (1)-6 | (1)-7 |
| Detergent composition (% by weight) | | | | | | | | | | | | | |
| Component (a) | Compound (1)-1 | 0.18 | 0.36 | 0.90 | 0.90 | 2.70 | | | | | | | 0.60 |
| | Compound (1)-2 | | | | | | 0.90 | | | | | | |
| | Compound (1)-3 | | | | | | | 0.90 | | | | | |
| Component (b) | Compound (1)-4 | 0.02 | 0.03 | 0.06 | 0.06 | 0.18 | | | | | | | 0.30 |
| | Compound (1)-5 | | | | | | 0.06 | | | | | | |
| | Compound (1)-6 | | | | | | | 0.06 | | | | | |
| | Compound (1)-7 | | 0.01 | 0.04 | 0.04 | 0.12 | | | | | | | 0.10 |
| | Compound (1)-8 | | | | | | 0.04 | | | | | | |
| | Compound (1)-9 | | | | | | | 0.04 | | | | | |
| Other surfactant | AES | 11.0 | 11.0 | 11.0 | 9.5 | 9.5 | 9.5 | 9.5 | 11.0 | 11.0 | 9.5 | 9.5 | 11.0 |
| | LAPB | 4.0 | 4.0 | 4.0 | | | | | | 4.0 | 4.0 | | 4.0 |
| | LDMAO | | | | 5.5 | 5.5 | 5.5 | 5.5 | | | 5.5 | 5.5 | |
| | DEA | | | | | | | | | | | 1.0 | |
| | MEA | | | | | | | | | 1.0 | | | |
| pH | | 6.0 | 6.0 | 6.0 | 7.5 | 7.5 | 7.5 | 7.5 | 6.0 | 6.0 | 7.5 | 7.5 | 6.0 |
| Foam volume (ml) | Immediately thereafter | 237 | 259 | 275 | 259 | 256 | 249 | 264 | 193 | 216 | 231 | 237 | 191 |
| | 5 minutes thereafter | 220 | 243 | 267 | 251 | 236 | 241 | 256 | 183 | 177 | 189 | 190 | 180 |

Comparative Example (2)-5

Various surfactant compositions having the formulations as shown in Table (2)-1 were prepared using the following components and their foamabilities were evaluated by the following method. The results are shown in Table (2)-1.

<Components>

Component (a)

Compound (2)-1: Same as the above-mentioned compound (1)-1

Compound (2)-2: Same as the above-mentioned compound (1)-2

Compound (2)-3: Same as the above-mentioned compound (1)-3

Component (b)

Compound (2)-4: Same as the above-mentioned compound (1)-7

Compound (2)-5: Same as the above-mentioned compound (1)-8

Compound (2)-6: Same as the above-mentioned compound (1)-9

Compound (2)-7: 2-(Methylamino)ethyl laurate

Compound (2)-8: (2-Ethylaminoethyl) coco-fatty carboxylate

Compound (2)-9: (2-Ethylaminoethyl) palm kernel-fatty carboxylate

Other Surfactants

AES, LAPB, LDMAO, MEA and DEA have the same meanings as defined above.

EAA: Polyoxyethylene(2) coconut oil-fatty acid monoethanolamide

<Method for Evaluating the Foamability (2)>

Foam volume (mL) immediately after the shaking was measured in the same manner as in the method for evaluating the foamability (1) except that a surfactant composition was used instead of the above-mentioned detergent composition.

TABLE (2)-1

| | | | Comparative Example (2)-5 |
|---|---|---|---|
| Surfactant composition (parts by weight) | Component (a) | Compound (2)-1 | |
| | | Compound (2)-2 | |
| | | Compound (2)-3 | |
| | Component (b) | Compound (2)-4 | |
| | | Compound (2)-5 | |
| | | Compound (2)-6 | |
| | | Compound (2)-7 | |
| | | Compound (2)-8 | |
| | | Compound (2)-9 | |
| | Other surfactant | AES | 11.0 |
| | | LAPB | 4.0 |
| | | LDMAO | |
| | | MEA | |
| | | DEA | |
| | | EAA | 1.0 |
| pH | | | 6.0 |
| Foam volume (ml) | | | 221 |

Examples (2)-8 to (2)-16 and Comparative Examples (2)-8 to (2)-11

Various surfactant compositions having the formulations as shown in Table (2)-2 were prepared using the components shown in Table (2)-2 and their foamabilities were evaluated in the same manner as in Example (2)-1. The results are shown in Table (2)-2.

TABLE ②-2

|  |  | Example |  |  |  |  |  |  |  |  | Comparative Example |  |  |  |
|---|---|---|---|---|---|---|---|---|---|---|---|---|---|---|
|  |  | ②-8 | ②-9 | ②-10 | ②-11 | ②-12 | ②-13 | ②-14 | ②-15 | ②-16 | ②-8 | ②-9 | ②-10 | ②-11 |
| Surfactant composition (parts by weight) | | | | | | | | | | | | | | |
| Component (a) | Compound ②-1 | 3.0 | 1.0 | 2.0 | 3.0 | | | | | | | | | |
| | Compound ②-3 | | | | | 2.0 | 2.0 | 3.0 | 4.0 | 4.0 | | | | |
| Component (b) | Compound ②-4 | 0.13 | 0.04 | 0.08 | 0.13 | | | | | | | | | |
| | Compound ②-6 | | | | | 0.06 | 0.21 | 0.35 | 0.12 | 0.48 | | | | |
| Other component | AES | 18.0 | 19.0 | 18.0 | 17.0 | 18.0 | 18.0 | 17.0 | 16.0 | 16.0 | 20.0 | 18.0 | 18.0 | 15.0 |
| | MEA | | | | | | | | | | | 2.0 | | |
| | DEA | | | | | | | | | | | | 4.0 | |
| | EAA | | | | | | | | | | | | | 5.0 |
| Glycerol | | 0.50 | 0.50 | 0.50 | | 0.20 | 0.30 | 0.40 | 0.40 | | | | | |
| Foam volume (ml) | | 212 | 238 | 246 | 236 | 208 | 219 | 250 | 243 | 257 | 190 | 199 | 198 | 193 |

Examples ②-17 to ②-20 and Comparative Examples ②-12 to ②-16

Various surfactant compositions having the formulations as shown in Table ②-3 were prepared using the components shown in Table ②-3 and they were measured in the viscosity at 25° C. using an ordinary Brookfield viscometer. The results are shown in Table ②-3.

TABLE ②-3

|  |  | Example |  |  |  | Comparative Example |  |  |  |  |
|---|---|---|---|---|---|---|---|---|---|---|
|  |  | ②-17 | ②-18 | ②-19 | ②-20 | ②-12 | ②-13 | ②-14 | ②-15 | ②-16 |
| Surfactant composition (parts by weight) | | | | | | | | | | |
| Component (a) | Component ②-1 | 5.0 | | | | | | | | |
| | Component ②-3 | | 5.0 | 5.0 | 5.0 | | | | | 4.0 |
| Component (b) | Component ②-4 | 0.20 | | | | | | | | |
| | Component ②-6 | | 0.15 | 0.35 | 0.60 | | | | | |
| Other surfactant | AES | 15.0 | 15.0 | 15.0 | 15.0 | 20.0 | 15.0 | 15.0 | 15.0 | 16.0 |
| | MEA | | | | | | 5.0 | | | |
| | DEA | | | | | | | 5.0 | | |
| | EAA | | | | | | | | 5.0 | |
| Glycerol | | 0.50 | 0.50 | 0.50 | 0.50 | | | | | |
| Viscosity (mPa · s) | | 8253 | 3813 | 4065 | 6698 | 12 | 1934 | 1725 | 163 | 1938 |

What is claimed is:

1. A surfactant composition containing a component (a) represented by the following formula (I) and at least one component (b) represented by the formulae (II) and (III), in their total amount of 0.1 to 80% by weight, at the ratio of (a)/(b) by weight of from 99.9/0.1 to 70/30;

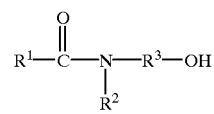

(I)

wherein $R^1CO-$ is a saturated or unsaturated acyl group which has 6 to 24 carbon atoms and which may have a hydroxy group; $R^2$ is a linear or branched alkyl group having 1 to 3 carbon atoms; and $R^3$ is a linear or branched alkylene group having 1 to 6 carbon atoms or alkenylene group having 2 to 6 carbon atoms;

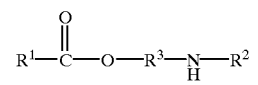
(II)

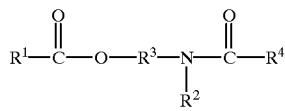
(III)

wherein $R^1CO-$, $R^2$ and $R^3$ have the same meanings as above and $R^4CO-$ is a saturated or unsaturated acyl group which has 6 to 24 carbon atoms and which may have a hydroxy group.

2. The composition as claimed in claim 1, which comprises a surfactant other than the above-mentioned components (a) and (b).

3. The composition as claimed in claim 1 or 2, wherein the ratio of the component (a) to the component (b), namely (a)/(b), by weight is from 99.99/0.01 to 80/20.

4. The composition as claimed in claim 1 or 2, wherein the blending ratios of the compounds (I), (III) and (II) to their total amount are 80 to 99.99% by weight of the compound (I), 0.01 to 20% by weight of the compound (III) and 0 to 5% by weight of the compound (II).

5. The composition as claimed in claim 2, wherein the ratio of the blending amount of the components (a) and (b) in total to the compounding amount of the surfactant other than the components (a) and (b) is from 0.5/99.5 to 50/50 by weight.

6. The composition as claimed in claim 1 or 2, which comprises glycerol as an essential component which is contained in an amount of 20% by weight or less as compared with the sum of the total amount of the components (a) and (b) and the amount of the surfactant other than the components (a) and (b).

7. The composition as claimed in claim 2, which comprises glycerol an essential component in an amount of 20% by weight or less as compared with the sum of the total amount of the components (a) and (b) and the amount of the surfactant other than the components (a) and (b), provided that the ratio of the blending amount of the components (a) and (b) and glycerol in total to the blending amount of the surfactant other than the components (a) and (b) is from 0.5/99.5 to 50/50 by weight.

* * * * *